United States Patent [19]
Gil et al.

[11] Patent Number: 5,631,032
[45] Date of Patent: May 20, 1997

[54] PROCESS FOR THE PREPARATION OF GROUND CEREAL BASED FOODS AND FOODSTUFFS OBTAINED THEREBY

[75] Inventors: Angel Gil, Esmeralda; Daniel Morales, Pulianas; Eduardo Valverde, El Serrallo, all of Spain

[73] Assignee: Union Industrial y Agro-Ganadera, S.A. (UNIASA), Granada, Spain

[21] Appl. No.: 415,224

[22] Filed: Mar. 31, 1995

Related U.S. Application Data

[63] Continuation of Ser. No. 320,766, Oct. 11, 1994, abandoned, which is a continuation of Ser. No. 987,556, Dec. 8, 1992, abandoned, which is a continuation of Ser. No. 686,474, Apr. 17, 1991, abandoned.

[51] Int. Cl.$^6$ ..................................................... A21D 2/00
[52] U.S. Cl. .............................. 426/28; 426/549; 426/466
[58] Field of Search ........................... 426/20, 28, 19, 426/466, 456, 455, 459, 460, 463, 465, 549

[56] References Cited

U.S. PATENT DOCUMENTS

| | | | |
|---|---|---|---|
| 128,342 | 6/1872 | Waitt | 426/466 X |
| 620,645 | 3/1899 | Dodd | 426/28 |
| 1,108,555 | 8/1914 | Deming | 426/28 |
| 1,395,831 | 11/1921 | Kelly | 426/466 X |
| 1,416,588 | 5/1922 | Swezey | 426/466 |
| 4,193,758 | 3/1980 | Peterson et al. | 426/466 X |
| 4,656,040 | 4/1987 | Fulger | 426/28 |
| 4,710,386 | 12/1987 | Fulger | 426/28 |
| 4,810,506 | 3/1989 | Lewis | 426/28 |
| 4,828,846 | 5/1989 | Rasco | 426/20 |
| 4,834,988 | 5/1989 | Karwowski | 426/28 |
| 4,834,989 | 5/1989 | Bolles | 426/28 |
| 4,857,339 | 8/1989 | Maselli | 426/28 |
| 4,859,474 | 8/1989 | Neidleman | 426/28 |
| 4,899,517 | 2/1990 | Shima et al. | 53/400 X |
| 4,996,063 | 2/1991 | Inglett | 426/28 |
| 5,013,561 | 5/1991 | Goering | 426/28 |
| 5,045,328 | 9/1991 | Lewis | 426/28 |
| 5,059,430 | 10/1991 | Bowles | 426/20 |
| 5,082,673 | 1/1992 | Inglett | 426/28 |
| 5,209,938 | 5/1993 | Kraus | 426/20 |
| 5,316,776 | 5/1994 | Annuk | 426/20 |
| 5,380,542 | 1/1995 | Jenkins | 426/28 |
| 5,387,426 | 2/1995 | Harris | 426/28 |
| 5,395,623 | 3/1995 | Kovach | 426/20 |

*Primary Examiner*—Carolyn Paden
*Attorney, Agent, or Firm*—Donald O. Nickey; Thomas D. Brainard

[57] ABSTRACT

Process for the preparation of ground cereal based foods and food products obtained thereby. The process comprises an initial phase of toasting all the cereals used and a hydrolyzation phase with amylolytic enzymes of the toasted cereals. The food products obtained have better organoleptic and hygienic properties, improved dispersibility, and allow reduction in the amount of edulcorants to be added.

7 Claims, No Drawings

PROCESS FOR THE PREPARATION OF GROUND CEREAL BASED FOODS AND FOODSTUFFS OBTAINED THEREBY

CROSS-REFERENCE TO RELATED APPLICATIONS

This application is a continuation of patent application Ser. No. 08/320,766, filed Oct. 11, 1994, now abandoned, which itself is a continuation of patent application Ser. No. 07/987,556, filed Dec. 8, 1992, now abandoned, which itself is a continuation of patent application Ser. No. 07/686,474, filed Apr. 17, 1991, also abandoned.

BACKGROUND OF THE INVENTION

The invention refers to a process for the preparation of foodstuffs in which the main component is cereals, as well as the food products obtained by this process, which as a result have better organoleptic (flavor/aroma) and hygienic properties, improved dispersibility, durable viscosity and a smaller amount of cariogenic sweeteners.

Cereals constitute an important group of the substances for human nourishment, though their nutritional task is particularly relevant during the very first years of the individual. Diets for breast-feeding babies, based on mother's milk or on the use of artificial milk formulas, are normally sufficient to cover the nutritional needs during the first six months of life, the cereals being usually the bridge towards an adult diet. The choice of cereal based foods or cereals with milk as the first element of complementary feeding during the second part of the first year of life is not an uncommon decision, since cereals are very useful in the development of the individual. Thus, they provide proteins and contribute immensely to the energy balance, due to their relatively high natural carbohydrates content, augmented by the addition of saccharose as the usual sweetener, although the cariogenic power of this sugar limits its use.

Another advantage of the consumption of cereals comes from the change introduced with regard to the source of energy. The use of cereals leads to a progressive reduction in the ingestion of milk and therefore the energy contribution provided by the fats, the presence of which is low in cereals. Thus, while fats provide 50% of the energy during the first months of life, towards the end of the first year they constitute only 25–30%. However, in order to cover the daily protein and calcium requirements, it is recommended that at least 500 ml of milk be consumed.

A further reason for using foods other than human milk and infants formulas, is to prevent iron deficiency, and from this point of view the supplementation of cereals with iron is readily accepted. However, organoleptic (flavor/aroma) problems arise from the addition of iron, the usual solution to which is to increase the amount of sweeteners added.

On this subject, the European Society of Gastroenterology and Pediatric Nutrition (ESPGAN), have set a regulation on the composition and use of cereals for breast-feeding babies (ESPGAN, Committee on Nutrition, Acta Paed. Scan. 287, 1981), including the adequate treatment for easy dispersion in water or milk and digestion.

With reference to the starch present in cereals, it is known that the activity of pancreatic amylase breast-feeding babies is low, particularly in the first months of life. Chemical processes have often been used to alter the structure of the links between amylase and amylopectin, producing the so-called modified starches. This modification provides an improvement in texture, consistency and flavor in the food, but there is concern regarding the toxic effects of these starches, generally added at a concentration of 5–6.5%, due to the presence of residual quantities of the chemical reagents used in the modification. The possible interference of modified starches on the absorption of minerals due to their chelation has also been reported.

Within the conventional process for the preparation of cereal based foods, there has been widely described and used the step of changing the structure of the starch by enzymatic hydrolysis, the generally employed enzymes being those of the group of alpha/beta-amylase and glucoamylase.

Basically, this conventional process comprises the stages of mixing the selected cereals with water, heating the mixture to temperatures equal or over 100° C., cooling the mixture, addition of enzymes for a treatment of hydrolysis for the whole mixture or a part thereof, and drying the mixture Said conventional process is completed, according to each case, with the stages of inactivating the enzymes by re-heating or addition of chemical reagents, pH adjustment of the mixture, addition of vitamins, minerals, edulcorants, fats, milk, fruits or vegetables, as well as the stages of forming the food as flakes, pellets or powder.

For example, in European patent 031050 there is described a process in which the mixture of starchy material and water is boiled to 150°–160° C. for 15–60 seconds, cooled to 50°–90° C. and then a 5% by weight of an alpha/beta-amylase is added which acts during 10–60 min. The resulting product is sterilized by steam at 115°–150° C. for 5–20 seconds and spray dried. European patents 258486 and 350952 also refer to enzymatic hydrolysis processes for cereal based preparations.

By following said conventional process, the boiling of the cereal mixture in water at temperatures about 100° C. only produces, most of the times, an uncomplete cooking of the cereals, what results in an undesired flavor/aroma for the product. This deteriminated result, together with the aforementioned ones, is sought to be remedied by adding sweeteners in quantities up to 40% by weight, thus increasing the undesirable cariogenic effects.

Also, when starch is heated in the presence of water, even in the drying phase, the gelification of the non-hydrolyzed starches takes place. This causes an affinity of the product to the collection of water, which in time provokes an increase in its viscosity and affects its dispersibility in water or milk.

Finally, food products obtained by this conventional process present hygienic inconvenients, since microbial development is favored during the mixture of cereals and water at some intervals of temperature.

SUMMARY OF THE INVENTION

Therefore, it is an objective of the invention to provide a process for the preparation of cereal based foods by which the resulting products, also an objective of the invention, present better flavor, aroma and dispersibility, improved hygienic properties and storage conditions, a medium range durable viscosity, without problems of syneresis and requiring smaller amounts of sweeteners added.

DESCRIPTION OF THE PREFERRED EMBODIMENTS

It is known that thermal treatments may have a sensible effect on the organoleptic (flavor/aroma/color/texture) and physical characteristics of foods. Sometimes these changes are beneficial, desirable and even necessary, but on other occasions they produce a deterioration in the basic raw material.

In the case of cereals, there has been described and used the toasting process as a final treatment, complementary or optional, for the product (flake, pellet) resulting from the process.

According to the present invention, a toasting treatment of the cereal, which confers to this material a particular and characteristic color, aroma and flavor widely appreciated, is performed over the initial raw material, that is, the ground cereal or mixture of ground cereals which will be submitted to the further process of preparation.

Said toasting treatment, besides the aforementioned characteristics, provides additional and noticeable advantages during the further process of preparation of the cereal based food by enzymatic hydrolysis.

Toasting causes a loss of moisture in the ground cereals and alters their proteinic structure, which means a modification in the structure of the starch granules and results in an increased action of the enzymes during the later process of hydrolysis.

However, when the hydrolysis process is favored there is obtained an increase of the glucose present in the carbohydrate mixture (glucose-maltodextrins-starch) of the product, increasing its sweet flavor and thus allowing a reduction in the amounts of cariogenic sweetners to be added.

Having taken into account that the carbohydrate mixture will then have more glucose and less non-hydrolyzed starch, the product will present an improved dispersibility, will keep its viscosity for longer periods of time and no syneresis will be produced when the product is prepared for ingestion.

Finally, the toasting treatment provides a drastic reduction of the microbial load usually present in ground cereals, thus making possible to work with a substantially sterile material which avoids microbial development during the later process of hydrolysis.

In practice, all cereals grains as well as certain roots (potato, arrow-root and tapioca) and some seeds (peanut, sesame or soy) may be used for the production of cereal based foods, which can be prepared as simple foods containing only one cereal, or as a complex made up of a mixture of the above-mentioned ingredients, with the possible addition of sugar, honey, fats, cocoa or the like; enriched with milk and other compounds with a high protein content, as well as vegetables and fruits, depending on the quantity and/or quality of protein desired. The diluting liquid is usually whole milk, infant formula or water.

In the process of the invention the selected cereal material will be present in ground form, the degree of grinding varying, according to the scope of the product, from a gross breaking to a fine powder.

The present invention relates to a process for the preparation of ground cereal based foods comprising the stages of selection and eventual mixing of different cereals, dispersion in water, boiling, heat drying, and addition of sweeteners, aromas and other food substances, which is characterized by submitting all the cereals, once they have been selected and eventually mixed, to a toasting process before their dispersion in water, and by submitting all the toasted cereals in dispersion to a hydrolysis process with amylolytic enzymes, the temperature of the dispersion being about 35°–60° C. where an enzyme or combination of amylolytic enzymes is added.

Preferably, the toasting process is carried out at a temperature of 120°–150° C. for 15–90 minutes approximately.

Preferably, the enzymatic hydrolysis reaction is maintained for a period of 10–90 minutes approximately, and the concentration of enzyme or combination of amylolytic enzymes is within the range of 0.2–4.0 g/kg of cereal approximately.

The invention also relates to the food products obtained by the process, which are characterized by being made up of ground cereals, all toasted and later hydrolyzed by amylolytic enzymes.

Preferably, the toasted cereals are hydrolyzed by amylolytic enzymes at a concentration of 0.2 to 4.0 g/kg of cereals approximately.

The cereal based foods thus obtained can be mixed or supplemented with other nourishing substances, such as milk, adapted milks and fruits, or even accompanied by cereals (grains, pellets, flakes) prepared by different methods.

A general non-limitative example of the process of the invention comprises the selection of a cereal or a mixture of cereals and their later toasting at 120°–150° C. for a period of 15–90 minutes in toasters heated with oil in closed circuit, followed by cooling to 20°–40° C. through a spiral conveyor with a double jacket for water circulation. The cereals toasted and cooled in this way are dispersed up to 20–40% of solids in water, in a tank with stirring and a double jacket. Next the temperature of the mixture is increased to 35°–60° C., and a dispersion of an alpha-amylase enzyme prepared in a small volume of water is added. The hydrolysis reaction is maintained for 10–90 minutes. The concentration of the enzyme used is between 0.2–4.0 g/kg of cereals and preferably between 0.2–2.0 g/kg.

Once the enzymatic reaction time is up, the resulting mass is submitted to a thermal treatment at 105°–130° C. for a period of 5 seconds to 2 minutes, so that the enzyme is inactivated and the gelification of the non-hydrolyzed starches also takes place. This treatment is carried out in a tubular heat-exchanger with scraped walls from which a rotating drier is fed. From here a sheet of the convenient thickness and dampness is obtained. Lastly, the agglomerated portions of dry cereal dough are sieved and then forwarded to the area of mixing and packing, where they are mixed only with sugar or with sugar and adapted milk, with the addition of a vitamin and mineral complex and an aroma, for example vanilla, as well as dehydrated fruit juice and whole fruit concentrates in the case of cereals with fruit.

Below appear non-limitative examples (Nos. 1–13) of compositions of cereal based foods prepared according to the process of the invention. Compositions are given in g/kg of final dry product, without moisture (w/m).

| Example No. 1: Food with seven cereals | |
|---|---|
| Wheat, rice, corn, soy, oats, barley and rye flours (w/m) | 821 |
| Enzyme | 0.2–3.0 |
| Sugar | 150–300 |
| Vitamin-mineral complex | 1 |
| Aroma | 0.5 |

Example No. 2:
Food with seven cereals and milk

| | |
|---|---|
| Wheat, rice, corn, soy, oats, barley and rye flours (w/m) | 514 |
| Enzyme | 0.2–3.5 |
| Sugar | 170–300 |
| Milk and dairy products | 347 |
| Vitamin-mineral complex | 1 |
| Aroma | 0.5 |

Example No. 3:
Cereal based food with fruits

| | |
|---|---|
| Wheat, rice, corn, soy, oats, barley and rye flours (w/m) | 809 |
| Enzyme | 0.3–2.5 |
| Sugar | 160–320 |
| Powdered apple | 2.0–5.0 |
| Powdered banana | 2.0–5.0 |
| Powdered orange | 2.0–5.0 |
| Vitamin-mineral complex | 1 |
| Aroma | 0.5 |

Example No. 4:
Cereal based food with fruits and milk

| | |
|---|---|
| Wheat, rice, corn, soy, oats, barley and rye flours (w/m) | 510 |
| Enzyme | 0.25–3.75 |
| Sugar | 150–300 |
| Milk and dairy products | 347 |
| Powdered apple | 1.5–3.5 |
| Powdered banana | 1.5–3.5 |
| Powdered orange | 1.5–3.5 |
| Vitamin-mineral complex | 1 |
| Aroma | 0.5 |

Example No. 5:
Cereal based food without gluten

| | |
|---|---|
| Rice and corn flours (w/m) | 820 |
| Enzyme | 1–4.2 |
| Sugar | 150–300 |
| Vitamin-mineral complex | 1 |
| Aroma | 0.5 |

Example No. 6:
Cereal based food without gluten and with milk

| | |
|---|---|
| Rice and corn flours (w/m) | 494 |
| Enzyme | 0.25–3.75 |
| Sugar | 160–320 |
| Milk and dairy products | 377 |
| Vitamin-mineral complex | 1 |
| Aroma | 0.5 |

Example No. 7:
Cereal based food without gluten and with fruits

| | |
|---|---|
| Rice and corn flours (w/m) | 809 |
| Enzyme | 0.3–4.5 |
| Sugar | 200–400 |
| Powdered apple | 2.0–5.0 |
| Powdered banana | 2.0–5.0 |
| Powdered orange | 2.0–5.0 |
| Vitamin-mineral complex | 1 |
| Aroma | 0.5 |

Example No. 8:
Cereal based food without gluten and with fruits and milk

| | |
|---|---|
| Rice and corn flours (w/m) | 492 |
| Enzyme | 0.25–3.75 |
| Sugar | 160–320 |
| Milk and dairy products | 377 |
| Powdered apple | 1.5–3.5 |
| Powdered banana | 1.5–3.5 |
| Powdered orange | 1.5–3.5 |
| Vitamin-mineral complex | 1 |
| Aroma | 0.5 |

Example No. 9:
Cereal based food for infant development

| | |
|---|---|
| Rice, corn and soy flours (w/m) | 820 |
| Enzyme | 1–4.2 |
| Sugar | 150–300 |
| Vitamin-mineral complex | 1 |
| Aroma | 0.5 |

Example No. 10:
Cereal based food with milk for infant development

| | |
|---|---|
| Rice, corn and soy flours (w/m) | 516 |
| Enzyme | 0.25–3.75 |
| Sugar | 150–300 |
| Milk and dairy products | 347 |
| Vitamin-mineral complex | 1 |
| Aroma | 0.5 |

Example No. 11:
Rice based food

| | |
|---|---|
| Rice flour (w/m) | 790–850 |
| Enzyme | 1–4.2 |
| Sugar | 148–208 |
| Vitamin-mineral complex | 1 |
| Aroma | 0.5 |

Example No. 12:
Oats based food

| | |
|---|---|
| Oats flour (w/m) | 780–830 |
| Enzyme | 1–4.2 |
| Sugar | 168–218 |
| Vitamin-mineral complex | 1 |
| Aroma | 0.5 |

| Example No. 13: Wheat based food | |
| --- | --- |
| Wheat flour (w/m) | 795–855 |
| Enzyme | 1–4.2 |
| Sugar | 143–203 |
| Vitamin-mineral complex | 1 |
| Aroma | 0.5 |

We claim:

1. A process for the preparation of cereal based foods having an increased level of glucose, comprising the steps of:

a. selecting ground cereal grain, b. toasting said ground cereal grain before said ground cereal grain is dispersed in water, c. dispersing the toasted cereal grain in water to form a dispersion, d. subjecting said cereal dispersion to a hydrolysis process with at least one amylolytic enzyme prior to a boiling step in (e) below, thereby producing a hydrolyzed cereal grain having an increased level of glucose, e. subsequent to said hydrolysis, boiling said hydrolyzed cereal grain in water, f. drying said hydrolyzed cereal grain, and g. mixing said dried hydrolyzed cereal grain with at least one additive, wherein said additive is selected from sweeteners, aromas and food substances selected from the group comprising dairy products, infant formulas, vitamin complexes, mineral complexes, fruits, dehydrated fruit, juices and additional cereals.

2. Process, according to claim 1, wherein the toasting process is carried out at a temperature of about 120°–150° C. for 15–90 minutes approximately.

3. Process, according to claim 1, wherein the enzymatic hydrolysis reaction is carried out at a temperature of about 35°–60° C. and maintained for 10–90 minutes approximately.

4. Process, according to claim 1, wherein the concentration of enzyme or combination of amylolytic enzymes is within the range of about 0.2–4.0 g/kg of cereals.

5. A cereal based food made according to the process of claim 1.

6. A cereal based food, according to claim 5, wherein the toasted cereals are hydrolyzed by amylolytic enzymes in a concentration of about 0.2–4.0 g/kg of cereals.

7. A cereal based food, according to claim 5, accompanied by other nourishing substances.

* * * * *